(12) United States Patent
Ribery et al.

(10) Patent No.: US 7,488,709 B2
(45) Date of Patent: Feb. 10, 2009

(54) CLEANSING COMPOSITION IN THE FORM OF AN AEROSOL FOAM WITHOUT ANIONIC SURFACTANT, AND USES IN COSMETICS

(75) Inventors: Delphine Ribery, Levallois Perret (FR); Isabelle Penverne, Courbevoie (FR)

(73) Assignee: L'Oreal S.A., Paris (FR)

( * ) Notice: Subject to any disclaimer, the term of this patent is extended or adjusted under 35 U.S.C. 154(b) by 344 days.

(21) Appl. No.: 11/287,298

(22) Filed: Nov. 28, 2005

(65) Prior Publication Data

US 2006/0135392 A1 Jun. 22, 2006

Related U.S. Application Data

(60) Provisional application No. 60/635,960, filed on Dec. 15, 2004.

(30) Foreign Application Priority Data

Nov. 26, 2004 (FR) .................... 04 52773

(51) Int. Cl.
*A61K 7/00* (2006.01)
(52) U.S. Cl. .................. 510/276; 424/74; 424/400; 424/401; 424/735; 424/765
(58) Field of Classification Search .............. 510/276; 424/74, 400, 401, 735, 765
See application file for complete search history.

(56) References Cited

U.S. PATENT DOCUMENTS

| | | | | |
|---|---|---|---|---|
| 5,525,263 | A * | 6/1996 | Bimczok et al. | 510/128 |
| 5,550,225 | A | 8/1996 | Philippe | |
| 5,888,478 | A * | 3/1999 | Maurin | 424/45 |
| 6,391,863 | B1 | 5/2002 | Philippe et al. | |
| 6,395,258 | B1* | 5/2002 | Steer | 424/47 |
| 2002/0086039 | A1* | 7/2002 | Lee et al. | 424/401 |
| 2003/0022799 | A1 | 1/2003 | Alvarado et al. | |
| 2004/0022818 | A1* | 2/2004 | Cho et al. | 424/401 |

FOREIGN PATENT DOCUMENTS

| | | |
|---|---|---|
| DE | 198 18 737 | 4/1998 |
| EP | 0 566 438 A1 | 10/1993 |
| EP | 0 820 755 A2 | 1/1998 |
| EP | 1 340 485 A2 | 9/2003 |
| FR | 2 739 556 | 11/1997 |
| WO | WO 00/64404 | 11/2000 |
| WO | WO 2004/089320 A1 | 10/2004 |

OTHER PUBLICATIONS

European Search Report for EP 05 29 2116, counterpart to present application.
Porter, *Handbook of Surfactants*, Chapman and Hall, New York (1991), pp. 116-178.
French Search Report for French Priority Application No. 04/52773, issued Jul. 26, 2005.

* cited by examiner

*Primary Examiner*—Marc S Zimmer
*Assistant Examiner*—M. Reza Asdjodi
(74) *Attorney, Agent, or Firm*—Finnegan, Henderson, Farabow, Garrett & Dunner, LLP

(57) ABSTRACT

The present disclosure relates to foaming cleansing compositions without anionic surfactant, comprising, in a cosmetically acceptable medium:

a) greater than 2% by weight in terms of active material of a non-betaine amphoteric or zwitterionic surfactant, relative to the total weight of the composition, b) at least one non-ionic surfactant, c) at least one propellant.

The present disclosure also relates to aerosol devices containing such a composition and also to the use of these compositions in cosmetics or dermatology, for instance for cleansing keratin materials such as the skin, the hair or the scalp.

24 Claims, 1 Drawing Sheet

CLEANSING COMPOSITION IN THE FORM OF AN AEROSOL FOAM WITHOUT ANIONIC SURFACTANT, AND USES IN COSMETICS

This application claims benefit of U.S. Provisional Application No. 60/635,960, filed Dec. 15, 2004, the contents of which are incorporated herein by reference. This application also claims benefit of priority under 35 U.S.C. § 119 to French Patent Application No. 04 52773, filed Nov. 26, 2004, the contents of which are also incorporated by reference.

The present disclosure relates to a foaming cleansing composition without anionic surfactant, comprising, in a cosmetically acceptable aqueous medium:

a) greater than 2% by weight in terms of active material of a non-betaine amphoteric or zwitterionic surfactant, relative to the total weight of the composition, b) at least one non-ionic surfactant, and c) at least one propellant.

The present disclosure also relates to a device comprising this composition and also to the use of this composition in cosmetics or dermatology, for instance for cleansing keratin materials such as the skin, the hair or the scalp.

Self-foaming washing gels packaged in two-compartment aerosol devices currently exist on the body hygiene market. Shower products packaged in an aerosol device comprising a single compartment are also known.

One of the wishes of consumers is to have products that, in the same action, provide cleansing and care of the skin, while at the same time benefiting from the pleasure provided by an abundant foam that rinses out easily. The presentation of cleansing products in an aerosol makes it possible, by virtue of the propellant, to rapidly generate, by pressing a button, an abundant foam that is then spread out over the body.

The rigidity of the foam generated at the outlet of the aerosol is an important characteristic. This is because it is this which will give the consumer, when it is taken up in the hand and spread out, a feeling of denseness and of a care effect.

Shower products provided in an aerosol exist on the market. These products all contain anionic surfactants which produce a compact, highly dense foam but which may have the drawback of also posing, because of the presence of the anionic surfactants, problems with tolerance with respect to the skin and/or the hair in certain individuals who have atopic or sensitive and/or dry skin.

In U.S. Pat. No. 6,395,258, it has already been proposed to produce relatively non-foaming gentle washing products in the form of an aerosol based on non-ionic surfactants, on an emollient of the fatty alcohol type, on another type of emollient, on a moisturizer and on a water-soluble propellant (nitrogen oxide). These products are intended to produce a very-low-density foam which does not require rinsing with water.

International Patent Application No. WO 00/64404 has already proposed conditioning shampoos in the form of an aerosol foam without anionic surfactant, wherein the washing base contains at least one non-ionic surfactant, in particular of the N-methyl alkyl alkylglucamide type, and, optionally, a betaine-type amphoteric surfactant.

German Patent Application No. DE 198 18 737 also discloses an example of a conditioning shampoo in the form of an aerosol foam containing a washing base without anionic surfactant, comprising 2% of cocoamphoacetate, 3% of cocoamidopropylbetaine, 5% of laureth-16 and 5% of alkylpolyglucoside and a propellant system consisting of a hydrocarbon and of carbon dioxide.

None of these documents is concerned with being able to produce an abundant rigid foam that can be readily rinsed with water, which will provide the consumer, when it is taken up in the hand and spread out, with a feeling of denseness and of a care effect.

There exists therefore the need to produce mild cleansing compositions for keratin materials, for instance the skin, in the form of an aerosol foam, wherein the washing base comprises no anionic surfactant and which can produce, at the outlet of the aerosol device, a foam that is as abundant as and can be as readily removed with water as those produced by the aerosol detergent compositions based on anionic surfactants currently on the market, without one or more of the drawbacks of tolerance with respect to the skin and/or the hair stated above.

The present inventors have found, surprisingly, that it is possible to overcome at least one of these drawbacks by using a composition comprising a washing base comprising greater than 2% by weight in terms of active material, relative to the total weight of the composition, of at least one non-betaine amphoteric or zwitterionic surfactant and of at least one non-ionic surfactant.

The compositions according to the present disclosure thus obtained may exhibit excellent tolerance with respect to the skin, the hair and/or the mucous membranes. They may also produce, at the outlet of the aerosol device, an abundant rigid foam that can be readily rinsed with water, which will provide the consumer, when it is taken up in the hand and spread out, a feeling of denseness and of a care effect.

This discovery forms the basis of the present disclosure.

The present disclosure thus relates to a foaming cleansing composition without anionic surfactant, comprising, in a cosmetically acceptable aqueous medium:

a) greater than 2% by weight in terms of active material of at least one non-betaine amphoteric or zwitterionic surfactant, relative to the total weight of the composition, b) at least one non-ionic surfactant, and c) at least one propellant.

A subject of the present disclosure is also an aerosol device comprising, in the same compartment, a foaming composition.

Another subject of the present disclosure is the use of the presently disclosed composition as a cleansing and/or make-up-removing product for keratin materials.

Another subject of the present disclosure is a method of cleansing keratin materials, comprising producing a foam at the outlet of an aerosol device in which the composition of the disclosure is packaged, and applying it to the keratin materials and then, after an optional application time, rinsing the keratin materials.

Figure 1:
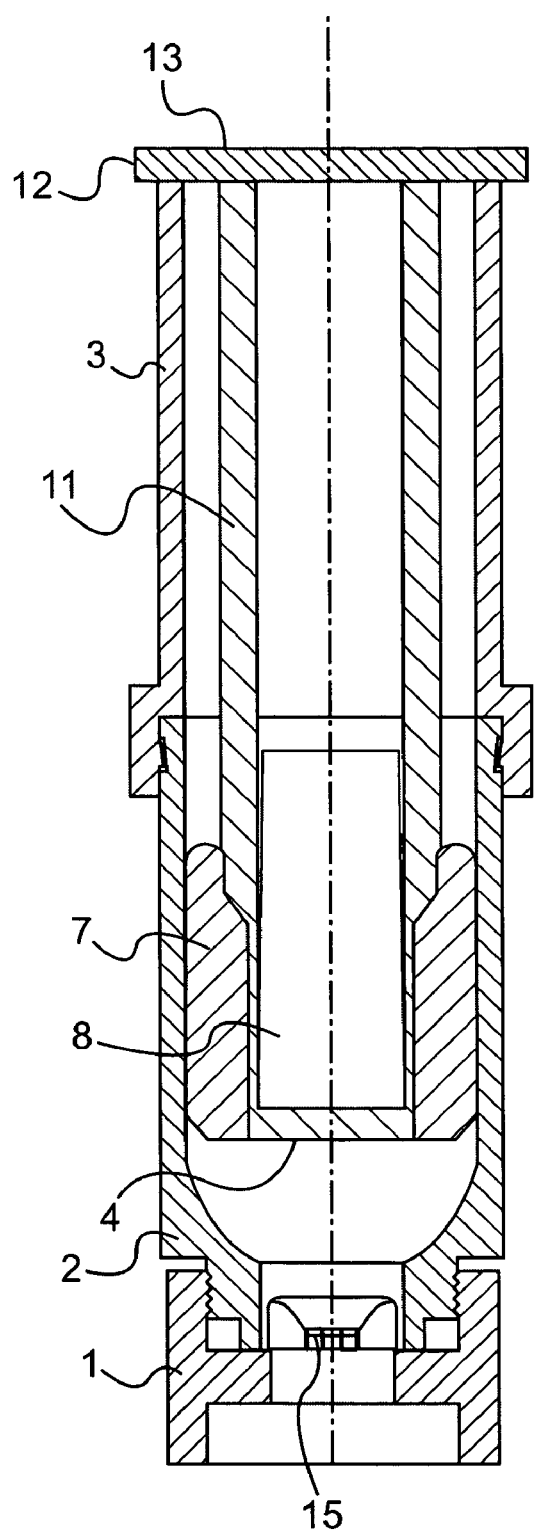
FIG. 1 represents a device for measuring the rigidity of a foam.

As used herein, the term "composition without anionic surfactant" is understood to mean any composition comprising less than 5% by weight of anionic surfactant, such as less than 1% by weight, or even being completely devoid of anionic surfactant.

As used herein, the term "betaine amphoteric or zwitterionic surfactant" is understood to mean alkylbetaines, N-alkylamidobetaines and derivatives thereof, sultaines, or mixtures thereof.

As used herein, the term "keratin materials" is understood to mean the skin (body and face), the scalp and the hair.

The cleansing compositions of the present disclosure can be packaged in aerosol devices in the presence of any propellant normally used for preparing aerosol compositions. Non-limiting mention may be made, for example, of hydrocarbon-based gases, for instance propane, n-butane, isobutane and mixtures thereof; fluorinated gases, for instance chlorodifluoromethane, dichlorodifluoromethane, difluoroethane, chlorodifluoroethane, dichlorotetrafluoroethane, etc., and mixtures thereof; hydrofluorocarbon-based gases; dimethyl ether and mixtures of dimethyl ether with at least one hydrocarbon-based gas; nitrogen, air and carbon dioxide, and mixtures thereof, can also be used as propellant gases in the present disclosure. In at least one embodiment, hydrocarbon-based gases comprising from 2 to 6 carbon atoms, and for instance a mixture of isobutane, propane and n-butane, are used in the present disclosure.

The propellant gas(es) is(are) present in the device in an amount ranging from 0.1 to 15% by weight, and for example 1 to 8% by weight, relative to the total weight of the composition.

The composition of the present disclosure may result in foams comprising a high rigidity that provides the user with a feeling of denseness when taken up in the hand. The foaming compositions in accordance with the present disclosure may produce, at the outlet of the aerosol device, a foam having a rigidity of greater than 25 s, and for instance greater than 50 s, the rigidity being measured according to the following device and method.

DETAILED DESCRIPTION OF THE DRAWING: RIGIDITY MEASURING DEVICE

The measuring device described in FIG. 1 comprises a transparent vertical Perspex cylinder 50 mm in diameter, composed of three main parts: a plinth 1 pierced with a hole 24 mm in diameter, on which is placed a valve 15, a lower cylindrical body 2, 104 mm in height, screwed onto the plinth, and an upper cylindrical body 3, 95 mm in height, screwed onto the lower body 2 so as to extend it axially, thus forming a vertical cylindrical housing open at its upper end.

The measuring device also comprises a movable piece that slides into the cylindrical housing. It is comprised of an upper stop 12 made of PVC from which two stainless steel piston suspension posts 11 descend. The stop 12 comprises a disc having a diameter greater than that of the cylindrical housing. The suspension posts are attached to the stop by means of two screws 13 that, at their lower end, are driven into a PVC piston 4 that weighs 119.3 g and is 45 mm in diameter. Placed in this piston is a stainless steel ballast piece 8, that weighs 225 g and is 58.6 mm in length. The piston comprises PVC guide blades 7 evenly distributed at its periphery and extending radially. The blades are suitable for guiding the piston along the axis of the cylindrical housing.

Method for Measuring Rigidity Using the Measuring Device Described Above

An aerosol device to be tested is placed in a water bath at 20±1° C. for an hour and a half. After this aerosol device has been shaken up and down five times, it is 5%-discharged so as to obtain a degree of filling of the aerosol device of 95%. The valve of the aerosol device to be tested is then locked onto the valve placed in the plinth of the lower body of the measuring device in order to fill the cylindrical housing with foam. This operation should be carried out without including air. The upper surface of the cylindrical housing is then leveled off. The upper body is then screwed to the lower body. The movable piece which comprises the ballast is introduced into the cylindrical housing from the open end. When the bottom of the movable piece is in contact with the foam, the timing device is initiated. The timing device is stopped when the movable piece has stopped descending, i.e. when the stop 12 comes into contact with the top of the upper body.

The rigidity is measured by the time, in seconds, that the movable piece takes to descend in the cylindrical housing.

The non-betaine amphoteric or zwitterionic surfactants in accordance with the present disclosure may be chosen from alkyl polyaminocarboxylates (APACs), alkylamphoacetates and mixtures thereof.

As alkyl polyaminocarboxylates (APACs), non-limiting mention may be made of sodium cocoylpolyaminocarboxylate, sold under the name Ampholak 7 CX/C® and Ampholak 7 CX® by the company Akzo Nobel; sodium stearylpolyamidocarboxylate sold under the name Ampholak 7 TX/C® by the company Akzo Nobel; sodium carboxymethyloleylpolypropylamine, sold under the name Ampholak XO7/C® by the company Akzo Nobel.

As alkylamphoacetates, non-limiting mention may for example be made of N-disodium N-cocoyl-N-carboxymethoxyethyl-N-carboxymethylethylenediamine (CTFA name: disodium cocoamphodiacetate), such as the product sold under the name Miranol C2M Concentre NP® by the company Rhodia Chimie; and N-sodium N-cocoyl-N-hydroxyethyl-N-carboxymethylethylenediamine (CTFA name: sodium cocoamphoacetate).

In one embodiment of the present disclosure, alkylamphoacetates can be used, for example of disodium cocoamphodiacetate, such as the product sold under the trade name Miranol® C2M Concentre NP® (solution containing 39% of active material) by the company Rhodia.

The compositions according to the present disclosure also comprise at least one non-ionic surfactant. These are compounds well known in themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols and fatty acids that are polyethoxylated, polypropoxylated or polyglycerolated and have a fatty chain comprising, for example, from 8 to 18 carbon atoms, it being possible for the number of ethylene oxide or propylene oxide groups to range from 2 to 50, and for the number of glycerol groups to range from 2 to 30. Maltose derivatives may also be mentioned. Non-limiting mention may also be made of copolymers of ethylene oxide and of propylene oxide, condensates of ethylene oxide and of propylene oxide with fatty alcohols; polyethoxylated fatty amides comprising, for example, from 2 to 30 mol of ethylene oxide, polyglycerolated fatty amides comprising, for example, from 1 to 5 glycerol groups, such as from 1.5 to 4; polyethoxylated fatty amines comprising, for example, from 2 to 30 mol of ethylene oxide; ethoxylated fatty acid esters of sorbitan comprising from 2 to 30 mol of ethylene oxide; fatty acid esters of sucrose, fatty acid esters of polyethylene glycol, ($C_6$-$C_{24}$) alkylpolyglycosides, N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

Alkylpolyglucosides that are used are those comprising an alkyl group comprising from 6 to 30 carbon atoms, and for instance from 8 to 16 carbon atoms, and comprising a hydrophilic (glucoside) group comprising 1, 2 or 3 saccharide units. Among these alkylpolyglucosides, non-limiting mention may be made of decylglucoside ($C_9$/$C_{11}$ alkylpolyglucoside (1.4)) such as the product sold under the name Mydol 10® by the company Kao Chemicals, under the name Plantaren 2000 UP® by the company Cognis, and under the name Oramix NS 10® by the company Seppic; caprylyl/capryl glucoside such as the product sold under the name Oramix CG 110® by the company Seppic; laurylglucoside such as the product sold under the names Plantaren 1200 N® and Plantacare 1200® by the company Cognis; and cocoglucoside such as the product sold under the name Plantacare 818/UP® by the company Cognis.

The maltose derivatives are, for example, those described in European Patent Application Publication No. EP-A-566438, such as O-octanoyl-6'-D-maltose, or else the O-dodecanoyl-6'-D-maltose described in French Patent FR-2,739,556.

Among the polyglycerolated fatty alcohols, non-limiting mention may be made of polyglycerolated dodecanediol (3.5 mol of glycerol), a product produced under the name Chimexane NF® by the company Chimex.

Fatty acid esters of polyethylene glycol may be chosen, for example glycerolated esters of polyethylene glycol, for instance the mixture PEG-7 Glyceryl Cocoate/PEG-200 Hydrogenated Glyceryl Palmate (CTFA name), such as the commercial product Rewoderm LI S80 by the company Degussa Care Specialties.

According to one embodiment of the present disclosure, the composition also comprises a betaine-type surfactant.

The betaines are, in at least one embodiment, chosen from alkylbetaines, N-alkylamidobetaines and derivatives thereof, sultaines or mixtures thereof.

Among the alkylbetaines, non-limiting mention may, for example, be made of cocobetaine, such as the product sold under the name Dehyton AB-30® by the company Cognis; laurylbetaine, such as the product sold under the name Genagen KB® by the company Clariant; oxyethylenated (10 EO) laurylbetaine, such as the product sold under the name Laurylether (10 OE) Betaine® by the company Shin Nihon Rica; oxyethylenated (10 EO) stearylbetaine, such as the product sold under the name Stearylether (10 OE) Betaine® by the company Shin Nihon Rica.

Among the N-alkylamidobetaines and derivatives thereof, non-limiting mention may, for example, be made of the cocoamidopropylbetaine sold under the name Lebon 2000 HG® by the company Sanyo, or under the name Empigen BB® by the company Albright & Wilson; the lauramidopropylbetaine sold under the name Rewoteric AMB12P® by the company Witco.

Among the sultaines, non-limiting mention may be made of the cocoylamidopropylhydroxysulfobetaine sold under the name Crosultaine C-50® by the company Croda.

In one embodiment of the present disclosure, cocobetaine can be used such as the product sold under the name Dehyton AB-30® by the company Cognis.

The total amount of amphoteric and non-ionic surfactant(s) by weight of active material can be greater than 5% by weight, relative to the total weight of the composition. It can range from 5.1 to 50% by weight for example, from 6 to 50% by weight, such as from 6 to 30% by weight, for instance from 8 to 25% by weight, relative to the total weight of the composition.

The cosmetically acceptable aqueous medium of the compositions of the disclosure may comprise, besides water, at least one solvent chosen from lower alcohols comprising from 1 to 6 carbon atoms, such as ethanol; polyols such as glycerol; glycols such as butylene glycol, isoprene glycol or propylene glycol, or polyethylene glycols such as PEG-8; sorbitol; sugars such as glucose, fructose, maltose, lactose or sucrose; and mixtures thereof. The amount of solvent(s) in the composition of the disclosure can range from 0.5 to 30% by weight, and for example from 5 to 20% by weight, relative to the total weight of the composition. As for water, the composition may comprise, for example, from 50 to 95% by weight of water relative to the total weight of the composition.

The compositions of the present disclosure can also comprise adjuvants normally used in the cosmetics field, and for instance those used in cleansing products. As adjuvants, non-limiting mention may, for example, be made of fragrances, preserving agents, sequestering agents (EDTA), pigments, pearlescent agents or opacifiers, mattifying, whitening or exfoliant, mineral or organic fillers, soluble dyes, cosmetic or dermatological active agents, non-ionic polymers such as polyvinylpyrrolidone (PVP), anionic polymers, cationic polymers, fatty substances such as oils or waxes. The amounts of these various adjuvants are those conventionally used in the field under consideration, and are, for example, from 0.01 to 20% of the total weight of the composition. These adjuvants and also the concentrations thereof should be such that they do not modify the property desired for the composition of the disclosure.

As examples of an oil, non-limiting mention may be made of oils of plant origin (jojoba, avocado, sesame, sunflower, maize, soya, safflower, grapeseed), mineral oils (petroleum jelly, optionally hydrogenated isoparaffins), synthetic oils (isopropyl myristate, cetearyl octanoate, polyisobutylene, ethylhexyl palmitate, alkyl benzoates), volatile or non-volatile silicone oils such as polydimethylsiloxanes (PDMSs) and cyclodimethylsiloxanes or cyclomethicones, and fluoro or fluorosilicone oils, and also mixtures of these oils.

As a cationic polymer, non-limiting mention may be made of the following polymers:

Polyquaternium 5 such as the product MERQUAT 5 sold by the company Calgon;

Polyquaternium 6 such as the product SALCARE SC 30 sold by the company Ciba, and the product MERQUAT 100 sold by the company Calgon;

Polyquaternium 7 such as the products MERQUAT S, MERQUAT 2200 and MERQUAT 550 sold by the company Calgon, and the product SALCARE SC 10 sold by the company Ciba;

Polyquaternium 10 such as the product Polymer JR400 sold by the company Amerchol;

Polyquaternium 11 such as the products GAFQUAT 755, GAFQUAT 755N and GAFQUAT 734 sold by the company ISP;

Polyquaternium 15 such as the product ROHAGIT KF 720 F sold by the company Rohm;

Polyquaternium 16 such as the products LUVIQUAT FC905, LUVIQUAT FC370, LUVIQUAT HM552 and LUVIQUAT FC550 sold by the company BASF;

Polyquaternium 22 such as the product MERQUAT 280 sold by the company Calgon;

Polyquaternium 28 such as the product STYLEZE CC 0 sold by the company ISP;

Polyquaternium 39 such as the product MERQUAT Plus 3330 sold by the company Calgon;

Polyquaternium 44 such as the product LUVIQUAT Care sold by the company BASF;

Polyquaternium 46 such as the product LUVIQUAT HOLD sold by the company BASF;

Polyquaternium 47 such as the product MERQUAT 2001 sold by the company Calgon.

As a cationic polymer, use may also be made of cationic guars, such as the product JAGUAR sold by the company Rhodia.

As active agents, any active agent which is normally used in the cosmetics and dermatological fields may be used, for instance water-soluble or liposoluble vitamins or provitamins such as vitamins A (retinol), C (ascorbic acid), B3 or PP (niacinamide), B5 (panthenol), E (tocopherol), K1, beta-carotene, and derivatives of these vitamins and for example their esters; steroids such as DHEA and 7α-hydroxy DHEA; antiseptics; antiseborrhoeic agents and antimicrobial agents, such as benzoyl peroxide, salicylic acid, triclosan, tricarban, azelaic acid; moisturizers such as glycerol, hyaluronic acid, pyrrolidonecarboxylic acid (PCA) and its salts, sodium pidolate, serine, xylitol, trehalose, ectoin, ceramides, urea; keratolytic and anti-ageing agents such as alpha-hydroxy acids, for instance glycolic acid, citric acid, lactic acid, beta-hydroxy acids, such as salicylic acid and its derivatives; enzymes and coenzymes, and for example coenzyme Q10; sunscreens; optical brighteners; slimming active agents such as caffeine, theophyline, theobromine, anti-inflammatories such as 18-β-glycyrrhetinic acid and ursolic acid, and mixtures thereof. In at least one embodiment of the present disclosure, a mixture of two or more of these active agents may be used. The active agent(s) may, for example, be present in an amount ranging from 0.01 to 20%, such as from 0.1 to 10%, and for example 0.5 to 5%, of the total weight of the composition.

As fillers, non-limiting mention may be made of mineral fillers such as talc or magnesium silicate (particle size: 5 microns) sold under the name Luzenac 15 M00® by the company Luzenac, kaolin or aluminium silicate such as, for example, that sold under the name Kaolin Supreme® by the company Imerys, or organic fillers such as starch, for instance the product sold under the name Amidon De Mais B® by the company Roquette, Nylon microspheres such as those sold under the name Orgasol 2002 UD NAT COS® by the company Atochem, expanded microspheres based on a copolymer of vinylidene chloride/acrylonitrile/methacrylonitrile comprising isobutane, such as those sold under the name Expancel 551 DE® by the company Expancel. It is also possible to add to the composition of the disclosure, fibers such as, for example, nylon fibers (Polyamide 0.9 DTEX 0.3 MM sold by the Etablissements Paul Bonte), cellulose fibers or "Rayon" (Rayon Flock RCISE NOOO3 MO4® sold by the company Claremont Flock Corporation).

As pearlescent agents or opacifiers, non-limiting mention may be made of sodium palmitate or magnesium palmitate, sodium stearate and hydroxystearate or magnesium stearate and hydroxystearate, acylated derivatives comprising a fatty chain, such as ethylene glycol monostearate or distearate or polyethylene glycol monostearate or distearate, ethers comprising fatty chains, for instance distearyl ether or 1-(hexadecyloxy)-2-octadecanol, fatty alcohols, for example stearyl alcohol, cetyl alcohol, behenyl alcohol, and mixtures thereof.

The foaming compositions according to the present disclosure can be used in the cosmetics and dermatological fields, and they may constitute, in at least one embodiment, a cosmetic composition, such as cleansing or make-up-removing products for the skin (body, face, eyes), the scalp and/or the hair. They can be used for any type of skin (dry, normal, mixed or oily).

The compositions of the present disclosure can, for example, be used as a shower product; a bath product; as a hand cleansing product; as a shampoo; as a make-up-removing product for the eyes and/or the face.

Another subject of the present disclosure is the cosmetic use of the composition as defined above, as a cleansing and/or make-up-removing product for human keratin materials, and, for example, for the skin.

The compositions according to the present disclosure can also be used for the treatment of oily skin, for example by adding thereto active agents specific for the treatment of oily skin, such as antiseborrhoeic agents, for instance salicylic acid and its derivatives, azelaic acid, triclosan, tricarban, piroctone olamine, niacinamide (vitamin PP).

Another subject of the present disclosure is the use of the composition as defined above, for preparing a composition for use in the treatment of oily skin.

The compositions according to the present disclosure have a final pH of ranging from 3 to 10. For example, this pH ranges from 4 to 8. The pH can be adjusted to the desired value conventionally, by adding a base (organic or inorganic) to the composition, for example aqueous ammonia or a primary, secondary or tertiary (poly)amine, such as monoethanolamine, diethanolamine, triethanolamine, isopropanolamine or 1,3-propanediamine, or else by adding an inorganic or organic acid, for example a carboxylic acid such as, for example, citric acid.

Another subject of the present disclosure is an aerosol device comprising, in the same compartment, the foaming composition according to the present disclosure. According to a one embodiment of the present disclosure, the aerosol device is a single-compartment device wherein the foaming composition of the disclosure is packaged.

Another subject of the disclosure is a method of cleansing keratin materials, comprising producing a foam at the outlet of the aerosol device wherein the composition of the disclosure is packaged, and applying it to the keratin materials and then, after an optional application time, rinsing the keratin materials.

Other than in the operating examples, or where otherwise indicated, all numbers expressing amounts of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The following examples serve to illustrate the disclosure without, however, being limiting in nature. The amounts indicated are given as % by weight unless otherwise mentioned, and the names of the compounds are given either as chemical names or CTFA (International Cosmetic Ingredient Dictionary and Handbook) names.

| Ingredients | Ex 1 (comparative example) | Ex 2 (comparative example) | Ex 3 (inventive example) |
|---|---|---|---|
| DISODIUM COCOAMPHODIACETATE | 0 | 4.794 | 4.794 |
| PEG-200 HYDROGENATED GLYCERYL PALMITATE | 2.3265 | 0 | 2.3265 |
| PEG-7 GLYCERYL COCOATE | 0.6345 | 0 | 0.6345 |
| GLYCEROL | 0.94 | 0.94 | 0.94 |

-continued

| Ingredients | Ex 1 (comparative example) | Ex 2 (comparative example) | Ex 3 (inventive example) |
| --- | --- | --- | --- |
| SODIUM CHLORIDE | 0.9165 | 2.7542 | 1.8377 |
| SODIUM GLYCOLATE | 0 | 0.9588 | 0.9588 |
| ISOBUTANE | 3.36 | 3.36 | 3.36 |
| BUTANE | 1.44 | 1.44 | 1.44 |
| PROPANE | 1.2 | 1.2 | 1.2 |
| SEQUESTERING AGENT | qs | qs | qs |
| PRESERVING AGENTS | qs | qs | qs |
| WATER | qs 100 | qs 100 | qs 100 |

The rigidity of the foam at the outlet of the aerosol device was measured according to the measuring device and the method described above. The results are given in Table 1 below.

TABLE 1

| Composition | Rigidity (in seconds) |
| --- | --- |
| Example 1 with betaine and without alkylamphoacetate | 4 |
| Example 2 without non-ionic surfactant | 9 |
| Example 3 (inventive example) | 27 |

With the aerosol device according to the present disclosure (Example 3) comprising the non-betaine amphoteric surfactant/non-ionic surfactant combination according to the disclosure, a synergistic effect was observed in terms of the rigidity of the foam compared with the aerosol devices of the prior art comprising the amphoteric non-betaine or non-ionic surfactant alone.

What is claimed is:

1. A foaming cleansing composition without anionic surfactant, comprising, in a cosmetically acceptable aqueous medium:
   a) greater than 2% by weight in terms of active material of at least one non-betaine amphoteric or zwitterionic surfactant chosen from alkylamphoacetates, relative to the total weight of the composition,
   b) at least one non-ionic surfactant chosen from glycerolated esters of polyethylene glycol, and
   c) at least one propellant;
   wherein the total amount of amphoteric and non-ionic surfactants by weight of active material is greater than or equal to 5% by weight, relative to the total weight of the composition.

2. The composition according to claim 1, wherein the at least one propellant is chosen from hydrocarbon-based gases, fluorinated gases, hydrofluorocarbon-based gases, dimethyl ether, nitrogen, air and carbon dioxide, and mixtures thereof.

3. The composition according to claim 2, in which the at least one propellant is chosen from hydrocarbon-based gases comprising from 2 to 6 carbon atoms.

4. The composition according to claim 1, in which the at least one propellant is a mixture of isobutane, propane and n-butane.

5. The composition according to claim 1, wherein the at least one propellant is present in the composition in an amount ranging from 0.1 to 15% by weight relative to the total weight of the composition.

6. The composition according to claim 5, wherein the at least one propellant is present in an amount ranging from 1 to 8% by weight relative to the total weight of the composition.

7. The composition according to claim 1, wherein a foam comprising a rigidity of greater than 25 s is produced at the outlet of the aerosol device.

8. The composition according to claim 7, wherein the foam has a rigidity of greater than 50 s.

9. The composition according to claim 1, wherein the at least one non-betaine amphoteric or zwitterionic surfactant is disodium cocoamphodiacetate.

10. The composition according to claim 1, wherein the at least one non-ionic surfactant is the mixture PEG-7 Glyceryl Cocoate/PEG-200 Hydrogenated Glyceryl Palmate.

11. The composition according to claim 1, further comprising at least one betaine-type surfactant.

12. The composition according to claim 11, wherein the at least one betaine-type surfactant is chosen from alkylbetaines, N-alkylamidobetaines and derivatives thereof, sultaines and mixtures thereof.

13. The composition according to claim 11, wherein the at least one betaine-type surfactant is cocobetaine.

14. The composition according to claim 1, wherein the total amount of amphoteric and non-ionic surfactant(s) by weight of active material ranges from 5.1 to 50% by weight relative to the total weight of the composition.

15. The composition according to claim 14, wherein the total amount of amphoteric and non-ionic surfactant(s) by weight of active material ranges from 6 to 50% by weight relative to the total weight of the composition.

16. The composition according to claim 15, wherein the total amount of amphoteric and non-ionic surfactant(s) by weight of active material ranges from 6 to 30% by weight relative to the total weight of the composition.

17. The composition according to claim 16, wherein the total amount of amphoteric and non-ionic surfactant(s) by weight of active material ranges from 8 to 25% by weight relative to the total weight of the composition.

18. The composition according to claim 1, further comprising at least one cosmetic adjuvant chosen from fragrances, preserving agents, sequestering agents (EDTA), pigments, pearlescent agents or opacifiers, mattifying, whitening or exfoliant, mineral or organic fillers, soluble dyes, cosmetic or dermatological active agents, non-ionic polymers, anionic polymers and fatty substances.

19. A cosmetic process for cleansing and/or removing makeup from human keratin materials comprising applying a composition to the human keratin materials comprising, in a cosmetically acceptable aqueous medium:
   a) greater than 2% by weight in terms of active material of at least one non-betaine amphoteric or zwitterionic surfactant chosen from alkylamphoacetates, relative to the total weight of the composition,
   b) at least one non-ionic surfactant chosen from glycerolated esters of polyethylene glycol, and
   c) at least one propellant;
   wherein the total amount of amphoteric and non-ionic surfactants by weight of active material is greater than or equal to 5% by weight, relative to the total weight of the composition.

20. The foaming cleansing composition according to claim 1, wherein it is in the form of bath or shower product, a product for cleansing the hands, a shampoo, and/or a product for removing makeup from the eyes, the face and/or the lips.

21. A process for preparing a formulation for treating oily skin, comprising:

adding, to a composition comprising, in a cosmetically acceptable medium,
  a) greater than 2% by weight in terms of active material of at least one non-betaine amphoteric or zwitterionic su surfactant chosen from alkylamphoacetates, relative to the total weight of the composition,
  b) at least one non-ionic surfactant chosen from glycerolated esters of polyethylene glycol, and
  c) at least one propellant;
  wherein the total amount of amphoteric and non-ionic surfactants by weight of active material is greater than or equal to 5% by weight, relative to the total weight of the composition
at least one active agent for treating oily skin chosen from anti-seborrhoeic agents.

22. A cosmetic method for cleansing soiling residues from human keratin materials comprising
  applying to said human keratin materials, in the presence of water, a composition comprising, in a cosmetically acceptable medium,
    a) greater than 2% by weight in terms of active material of at least one non-betaine amphoteric or zwitterionic surfactant chosen from alkylamphoacetates, relative to the total weight of the composition,
    b) at least one non-ionic surfactant chosen from glycerolated esters of polyethylene glycol, and
    c) at least one propellant;
    wherein the total amount of amphoteric and non-ionic surfactants by weight of active material is greater than or equal to 5% by weight, relative to the total weight of the composition
  wherein an aerosol device is used such that the composition is applied as a foam formed at the outlet of the aerosol device,
  massaging the composition to form a foam on the keratin materials and
  removing the foam formed and the soiling residue by rinsing with water.

23. An aerosol device comprising at least one compartment comprising therein a foaming cleansing composition comprising, in a cosmetically acceptable medium,
  a) greater than 2% by weight in terms of active material of at least one non-betaine amphoteric or zwitterionic surfactant chosen from alkylamphoacetates, relative to the total weight of the composition,
  b) at least one non-ionic surfactant chosen from glycerolated esters of polyethylene glycol, and
  c) at least one propellant;
  wherein the total amount of amphoteric and non-ionic surfactants by weight of active material is greater than or equal to 5% by weight, relative to the total weight of the composition.

24. The aerosol device according to claim 23, comprising a single compartment in which the foaming composition is packaged.

* * * * *